United States Patent
Hsu et al.

(10) Patent No.: US 11,966,374 B2
(45) Date of Patent: Apr. 23, 2024

(54) MEDICAL CLINICAL DATA QUALITY ANALYSIS SYSTEM BASED ON BIG DATA

(71) Applicant: Serv Medical Pte. Ltd., Singapore (SG)

(72) Inventors: Chun-Chieh Hsu, Beijing (CN); Shiyu Zhang, Beijing (CN); Jiangjiu Huang, Beijing (CN); Yingxi Wang, Beijing (CN); Rashaad Nawaz Tawquir, Beijing (CN)

(73) Assignee: SERV MEDICAL PTE. LTD., Singapore (SG)

( * ) Notice: Subject to any disclaimer, the term of this patent is extended or adjusted under 35 U.S.C. 154(b) by 0 days.

(21) Appl. No.: 18/350,727

(22) Filed: Jul. 11, 2023

(65) Prior Publication Data
US 2024/0020284 A1   Jan. 18, 2024

(30) Foreign Application Priority Data
Jul. 12, 2022   (CN) .......................... 202210815839.5

(51) Int. Cl.
  *G06F 16/00*   (2019.01)
  *G06F 16/215*  (2019.01)
  *G16H 10/20*   (2018.01)
  *G16H 40/20*   (2018.01)

(52) U.S. Cl.
  CPC .......... *G06F 16/215* (2019.01); *G16H 10/20* (2018.01); *G16H 40/20* (2018.01)

(58) Field of Classification Search
  None
  See application file for complete search history.

(56) References Cited

U.S. PATENT DOCUMENTS

| | | | |
|---|---|---|---|
| 2015/0220868 A1* | 8/2015 | Elashoff | G16H 10/60 705/2 |
| 2019/0051405 A1* | 2/2019 | Doi | G16H 10/60 |
| 2019/0369120 A1 | 12/2019 | Rhyne et al. | |
| 2023/0197213 A1* | 6/2023 | Yuasa | G16H 40/20 705/3 |

FOREIGN PATENT DOCUMENTS

| | | |
|---|---|---|
| CN | 104766259 A | 7/2015 |
| CN | 104951894 A | 9/2015 |
| CN | 106485403 A | 3/2017 |

(Continued)

*Primary Examiner* — Bai D Vu
(74) *Attorney, Agent, or Firm* — EAGLE IP LIMITED (57) ABSTRACT

The present invention discloses a medical clinical data quality analysis system based on big data, which relates to the field of medical big data technologies. The present invention is used to solve the technical problems that multi-link classified acquisition cannot be carried out on medical behaviors, and the quality of clinical data cannot be analyzed and reflected at the front end, middle link, and tail end of management. In the present invention, authenticity data, compliance data, process data and conclusive data are comprehensively acquired in admission, hospitalization, and discharge links of medical clinical data quality management, which is conducive to implementing multi-link classified acquisition of clinical medical behaviors, thereby facilitating subsequent dynamic and orderly quality analysis and control of clinical data.

7 Claims, 3 Drawing Sheets

(56) References Cited

FOREIGN PATENT DOCUMENTS

| | | |
|---|---|---|
| CN | 107680680 A | 2/2018 |
| CN | 109523265 A | 3/2019 |
| CN | 110223782 A | 9/2019 |
| CN | 110415831 A | 11/2019 |
| CN | 110584618 A | 12/2019 |
| CN | 112907045 A | 6/2021 |
| CN | 112992343 A | 6/2021 |
| CN | 113331800 A | 9/2021 |
| CN | 113593686 A | 11/2021 |
| CN | 114566282 A | 5/2022 |
| CN | 114639478 A | 6/2022 |
| WO | 2013140489 A1 | 9/2013 |

* cited by examiner

MEDICAL CLINICAL DATA QUALITY ANALYSIS SYSTEM BASED ON BIG DATA

CROSS-REFERENCE TO RELATED APPLICATION

This application claims priority to, and the benefit of, Chinese Patent Application No. 202210815839.5 filed on 12 Jul. 2022. The entire contents of the foregoing application are hereby incorporated by reference for all purposes.

TECHNICAL FIELD

The present invention relates to the field of medical big data analysis technologies, and in particular, to a medical clinical data quality analysis system based on big data.

BACKGROUND OF THE INVENTION

Medical clinical data is not only large-scale, but also diverse, high-value, and fast-growing, which is fully in line with the characteristics of big data. Medical record quality control is an important means to ensure medical quality, and a medical record is also one of the important sources of clinical data. If the source is not properly checked, it will give rise to a series of problems later. With regard to the medical record, there are usually the problems such as untimely writing of a first progress note, incomplete operation records, inaccurate disease diagnosis and operation diagnosis, incomplete first page of medical records, lack of signature of a senior physician, and unclear indications for antibiotic use. In the era of big data and artificial intelligence, hospitals need to employ information technology for data quality control, data cleaning and data governance, and investigate and deal with the problems, such as missing of critical variables, data inconsistency, and failure to follow format specifications, in a timely manner.

In the prior art (CN104766259A), there is disclosed a medical clinical quality monitoring and evaluation system based on a single-disease model, the system including: a clinical data integration subsystem for sending case data acquired during an original diagnosis and treatment process of single diseases into a clinical record database; a data cleaning and standardization subsystem for selecting case data from the clinical record database and processing the data to form a single-disease evaluation database; a statistical analysis and evaluation algorithm subsystem for performing index calculation and comprehensive evaluation calculation on the received data; and a clinical quality management application subsystem responsible for displaying a comprehensive evaluation result obtained through calculations by the statistical analysis and evaluation algorithm subsystem. Through the invention, processing and statistical evaluation of clinical data in terms of clinical quality management are achieved, and a medical quality manager can truly, objectively, and comprehensively master, in real time, the quality of a diagnosis and treatment process of various diseases in various clinical departments. However, it is found, after researches, that there are the following technical problems: Multi-link classified acquisition cannot be carried out on medical behaviors, and the quality of clinical data cannot be analyzed and reflected at the front end, middle link, and tail end of management.

In view of the technical shortcomings in this regard, a solution is proposed now.

BRIEF SUMMARY OF THE INVENTION

An object of the present invention is to provide a medical clinical data quality analysis system based on big data, which is used to solve the technical problems in the prior art that multi-link classified acquisition cannot be carried out on medical behaviors, and the quality of clinical data cannot be analyzed and reflected at the front end, middle link, and tail end of management.

Authenticity data and compliance data of a patient in each clinical department at admission, and process data and conclusive data of the patient during hospitalization and at discharge are acquired, such that authenticity data, compliance data, process data, and conclusive data are comprehensively acquired in admission, hospitalization, and discharge links of medical clinical data quality management. Therefore, the technical problem that multi-link classified acquisition cannot be carried out on medical behaviors is solved.

A medical record quality coefficient reflecting the quality of clinical data at admission is obtained by performing integration and processing on an authenticity factor and a compliance factor, and a medical record qualification signal or a medical record disqualification signal is output after the medical record quality coefficient is compared with a threshold thereof, such that from the perspectives of authenticity and compliance, the quality of clinical data at admission is reflected truly and reliably; and an operating quality coefficient reflecting the quality of clinical data during hospitalization and at discharge is obtained by performing integration and processing on a process factor and a conclusion factor, and an operating qualification signal or an operating disqualification signal is output after the operating quality coefficient is compared with a threshold thereof, such that from the perspectives of process and conclusion, the quality of clinical data during hospitalization and at discharge is reflected truly and reliably. Therefore, the technical problem that the quality of clinical data cannot be analyzed and reflected at the front end, middle link, and tail end of management is solved.

The object of the present invention may be achieved by the following technical solutions.

A medical clinical data quality analysis system based on big data, including a clinical data acquisition module, an admission data analysis module, a course data analysis module, a medical record quality inspection module, an operating quality inspection module, and a medical big data server, where the clinical data acquisition module is configured to acquire authenticity data and compliance data of a patient in each clinical department at admission within a fixed period of time and authenticity data and compliance data of the patient after the fixed period of time, and send the authenticity data and the compliance data to the admission data analysis module and the medical big data server, and the clinical data acquisition module is further configured to acquire process data and conclusive data of the patient in each clinical department during hospitalization and at discharge within a fixed period of time and process data and conclusive data of the patient after the fixed period of time, and send the process data and the conclusive data to the course data analysis module and the medical big data server;

the admission data analysis module is configured to perform authenticity analysis and processing on the authenticity data of the patient in each clinical department at admission within the fixed period of time and the authenticity data of the patient after the fixed period of time to obtain an authenticity factor for the clinical department, and send the authenticity factor to the medical record quality inspection module, and the admission data analysis module is further configured to perform compliance analysis and processing on the compliance data of the patient in each clinical department at admission within the fixed period of time and the compliance data of the patient after the fixed period of time to obtain a compliance factor for the clinical department, and send the compliance factor to the medical record quality inspection module;

the course data analysis module is configured to perform process analysis and processing on the process data of the patient in each clinical department during hospitalization and at discharge within the fixed period of time and the process data of the patient after the fixed period of time to obtain a process factor for the clinical department, and send the process factor to the operating quality inspection module, and the course data analysis module is further configured to perform conclusive analysis and processing on the conclusive data of the patient in each clinical department during hospitalization and at discharge within the fixed period of time and the conclusive data of the patient after the fixed period of time to obtain a conclusion factor for the clinical department, and send the conclusion factor to the quality inspection module;

the medical record quality inspection module is configured to process the authenticity factor and the compliance factor of the clinical department to obtain a medical record quality coefficient, and compare the medical record quality coefficient with a threshold thereof, and output a medical record qualification signal when the medical record quality coefficient is greater than the threshold thereof, and output a medical record disqualification signal and send the medical record disqualification signal to the medical big data server when the medical record quality coefficient is less than or equal to the threshold thereof;

the operating quality inspection module is configured to process the process factor and the conclusion factor of the clinical department to obtain an operating quality coefficient, and compare the operating quality coefficient with a threshold thereof, and output an operating qualification signal when the operating quality coefficient is greater than the threshold thereof, and output an operating disqualification signal and send the operating disqualification signal to the medical big data server when the operating quality coefficient is less than or equal to the threshold thereof; and the medical big data server is configured to multiply a medical record quality coefficient corresponding to the medical record disqualification signal by an operating quality coefficient corresponding to the operating disqualification signal to obtain a comprehensive quality coefficient, and compare the comprehensive quality coefficient with a preset range thereof, and perform no processing when the comprehensive quality coefficient is greater than a maximum value in the preset range thereof, output a second-level quality control signal when the comprehensive quality coefficient is within the preset range thereof, and output a first-level quality control signal when the comprehensive quality coefficient is less than a minimum value in the preset range thereof.

Further, the fixed period of time is 12 hours, 24 hours, 48 hours, or 72 hours, and the authenticity data includes name, age, gender, identity card number, date of birth, marital status, ethnicity, and native place of the patient, the marital status including unmarried, married, divorced, and widowed; and the compliance data includes recorded international disease code, a name of a present medical history, a name of a principal diagnostic disease, and a diagnostic scheme.

A Specific Process of the Authenticity Analysis and Processing is as Follows:

in step 1, comparing the authenticity data of the patient in each clinical department at admission within the fixed period of time with the authenticity data of the patient after the fixed period of time, to obtain a frequency of occurrence of mistakes, an average time for rectifying mistakes for qualification, and a number of completions mistakes are rectified for qualification of the authenticity data; and in step 2, marking the frequency of occurrence of mistakes, the average time for rectifying mistakes for qualification, and the number of completions mistakes are rectified for qualification of the authenticity data as $Z_{pi}$, $Z_{gi}$, and $Z_{ci}$, respectively, where $i=1, \ldots, n$, and $n$ is a positive integer greater than 1; and performing processing to obtain an authenticity factor $Z_{si}$ for each clinical department.

A Specific Process of the Compliance Analysis and Processing is as Follows:

in step 1, comparing the compliance data of the patient in each clinical department at admission within the fixed period of time with the compliance data of the patient after the fixed period of time, to obtain a frequency of occurrence of violations, an average time for rectifying violations for qualification, and a number of completions violations are rectified for qualification of the compliance data; and in step 2, marking the frequency of occurrence of violations, the average time for rectifying violations for qualification, and the number of completions violations are rectified for qualification of the compliance data as $H_{pi}$, $H_{si}$, and $H_{ci}$, respectively, where $i=1, \ldots, n$, and $n$ is a positive integer greater than 1; and performing processing to obtain a compliance factor $H_{gi}$ for each clinical department.

Further, the mistakes in the authenticity data include incorrect filling, omissions, and filling in wrong items; and the violations in the compliance data include inconsistency between the international disease code and international classification of diseases ICD-10, mismatch between the present medical history and an actual medical history of the patient, inconsistency between the name of the principal diagnostic disease and a name of a disease to be treated, and mismatch between a name of an operation, an item to be tested, or a name of a drug to be used in the diagnostic scheme and the disease to be treated.

Further, the process data includes medications and test items of the patient during hospitalization and their corresponding expenses, and a name of an operation for the patient during hospitalization; and the conclusive data includes a total amount paid by the patient during hospitalization and the condition of the patient at discharge.

A Specific Process of the Process Analysis and Processing is as Follows:

in step 1, comparing the process data of the patient in each clinical department during hospitalization and at discharge within the fixed period of time with the process data of the patient after the fixed period of time, to obtain a total number of occurrences of errors, a total time for rectifying errors for qualification, and a number of completions errors are rectified for qualification of the process data; and in step 2, marking the total number of occurrences of errors, the total time for rectifying errors for qualification, and the number of completions errors are rectified for qualification of the process data as Gci, Gsi, and Ghi, respectively, where i=1, ..., n, and n is a positive integer greater than 1; and performing processing to obtain a process factor Gzi for each clinical department.

A Specific Process of the Conclusive Analysis and Processing is as Follows:

in step 1, comparing the conclusive data of the patient in each clinical department during hospitalization and at discharge within the fixed period of time with the conclusive data of the patient after the fixed period of time, to obtain a total number of occurrences of problems, a total time for rectifying problems for qualification, and a number of completions problems are rectified for qualification of the conclusive data; and in step 2, marking the total number of occurrences of problems, the total time for rectifying problems for qualification, and the number of completions problems are rectified for qualification of the conclusive data as Jci, Jsi, and Jhi, respectively, where i=1, ..., n, and n is a positive integer greater than 1; and performing processing to obtain a conclusion factor Jzi for each clinical department.

Further, the errors in the process data include inconsistency between the medications as well as the test items of the patient during hospitalization and their corresponding expenses, and inconsistency between the name of the operation for the patient during hospitalization and an official name of the operation; and the problems in the conclusive data include inconsistency between the total amount paid by the patient during hospitalization and an actual calculated total payment amount, and nonconformity of records of the patient's condition at discharge with writing specifications.

Further, the medical clinical data quality analysis system further includes a historical quality analysis module and a quality evaluation module, where the historical quality analysis module is configured to retrieve the comprehensive quality coefficient from the medical big data server, generate a histogram and a line graph for unit time-comprehensive quality coefficient with the unit time as the abscissa and the comprehensive quality coefficient as the ordinate, and send the histogram and the line graph to a mobile terminal, and the historical quality analysis module is further configured to calculate a rate of change in the comprehensive quality coefficient in adjacent unit time, and send the rate of change to the quality evaluation module; and the quality evaluation module is configured to match the rate of change in the comprehensive quality coefficient in adjacent unit time with a rate of change evaluation table stored in the quality evaluation module, to obtain a quality inspection evaluation result.

Further, the unit time is selected from 12 hours, 24 hours, 48 hours, or 72 hours; and in the rate of change evaluation table, when the rate of change is greater than 20%, the quality inspection evaluation result indicates excellent; when the rate of change is between 10% and 20%, the quality inspection evaluation result indicates good; when the rate of change is between 0% and 10%, the quality inspection evaluation result indicates pass; when the rate of change is between −10% and 0, the quality inspection evaluation result indicates fail; and when the rate of change is less than −10%, the quality inspection evaluation result indicates poor.

The Present Invention has the Following Beneficial Effects:

1. In the present invention, the authenticity data and the compliance data of the patient in each clinical department at admission, and process data and conclusive data of the patient during hospitalization and at discharge are acquired, such that authenticity data, compliance data, process data, and conclusive data are comprehensively acquired in admission, hospitalization, and discharge links of medical clinical data quality management, which is conducive to implementing multi-link classified acquisition of clinical medical behaviors, thereby facilitating subsequent dynamic and orderly quality analysis and control of clinical data.

2. In the present invention, the medical record quality coefficient reflecting the quality of clinical data at admission is obtained by performing integration and processing on the authenticity factor and the compliance factor, and the medical record qualification signal or the medical record disqualification signal is output after the medical record quality coefficient is compared with the threshold thereof, such that from the perspectives of authenticity and compliance, the quality of clinical data at admission is reflected truly and reliably, and medical errors and costs are reduced at the front end of quality management; and the operating quality coefficient reflecting the quality of clinical data during hospitalization and at discharge is obtained by performing integration and processing on the process factor and the conclusion factor, and the operating qualification signal or the operating disqualification signal is output after the operating quality coefficient is compared with the threshold thereof, such that from the perspectives of process and conclusion, the quality of clinical data during hospitalization and at discharge is reflected truly and reliably, and medical errors and costs are reduced at the middle link and tail end of quality management.

3. In the present invention, the medical record quality coefficient and the operating quality coefficient are processed to obtain the comprehensive quality coefficient, and different levels of quality control signals are output after the comprehensive quality coefficient is compared with the preset range thereof, such that when both a medical record signal and an operating signal indicate disqualification, a matching quality control signal is precisely output, which facilitates taking corresponding measures for rectification; the histogram and the line graph of unit time-comprehensive quality coefficient intuitively reflect the change trend of comprehensive quality of medical clinical data per unit time; and the quality inspection evaluation result is obtained by performing matching with the rate of change evaluation table, such that scoring and rectification are performed depending on quality inspection evaluation results, thereby reducing the rate of error in clinical data.

BRIEF DESCRIPTION OF THE DRAWINGS

In order to describe the technical solution in examples of the present invention or the prior art more clearly, the drawings which need to be used in the description of the examples or the prior art will be simply introduced below. Obviously, the accompanying drawings in the following description show merely some examples of the present invention, and a person of ordinary skill in the art may still derive other drawings according to these drawings without creative efforts.

DETAILED DESCRIPTION OF THE INVENTION

The technical solutions in the present invention will be described clearly and completely below with reference to embodiments. Obviously, the described embodiments are merely some of, rather than all of, the embodiments of the present invention. On the basis of the embodiments of the present invention, all the other embodiments obtained by those of ordinary skill in the art without creative efforts shall fall within the scope of protection of the present invention.

Embodiment 1

Figure 1:
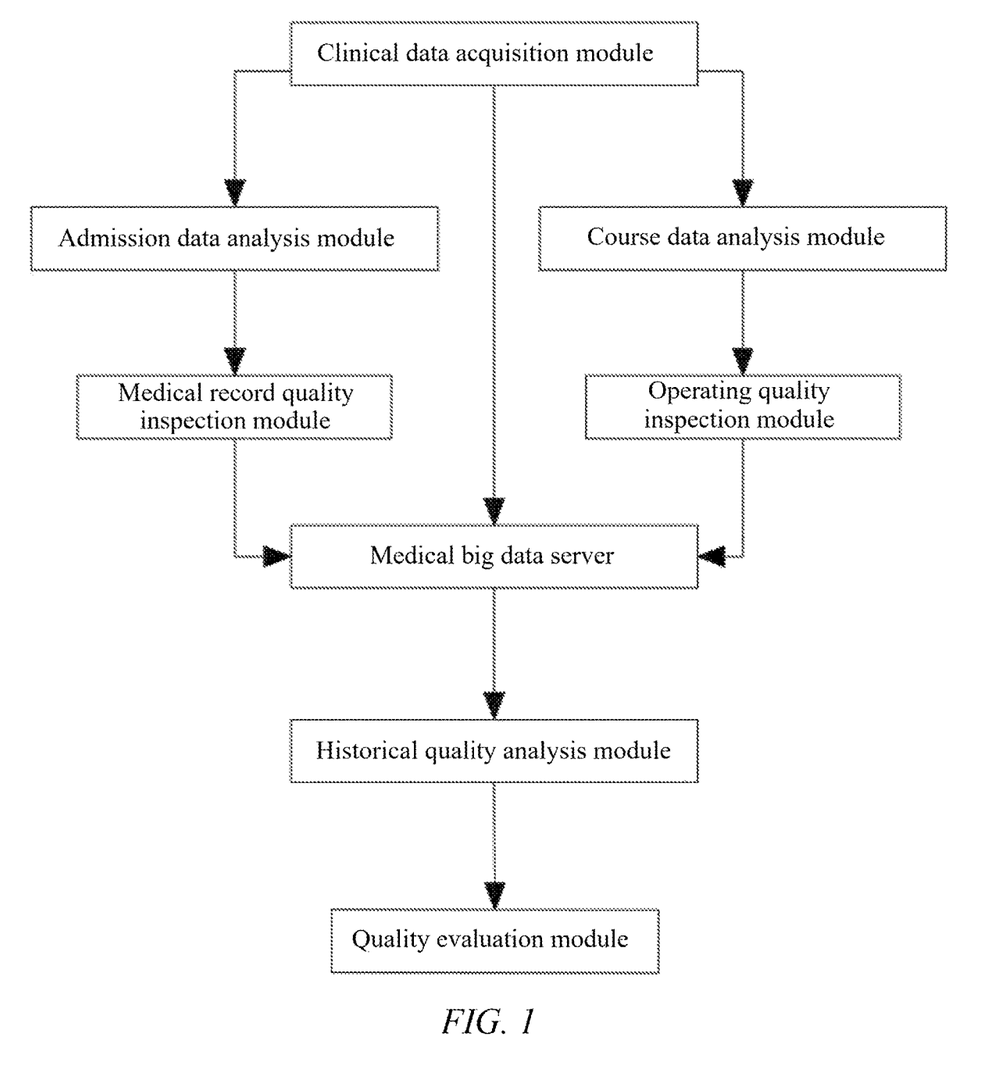
FIG. 1 is a frame diagram of a medical clinical data quality analysis system according to the present invention.

As shown in FIG. 1, this embodiment provides a medical clinical data quality analysis system based on big data, which is applied to hospitals or diagnosis and treatment institutions with a plurality of clinical departments. The system includes a clinical data acquisition module, an admission data analysis module, a course data analysis module, a medical record quality inspection module, an operating quality inspection module, a medical big data server, a historical quality analysis module, and a quality evaluation module. In one division mode, the clinical departments are divided into internal medicine, surgery, obstetrics and gynecology, pediatrics, andrology, oncology, dermatology, infectious diseases and psychiatry. Definitely, other division modes are not specifically limited in this embodiment, and the clinical departments are set and adjusted according to the actual situation of the hospitals or diagnosis and treatment institutions.

Specifically, the clinical data acquisition module is configured to acquire authenticity data and compliance data of a patient in each clinical department at admission within a fixed period of time and authenticity data and compliance data of the patient after the fixed period of time, and send the authenticity data and the compliance data to the admission data analysis module and the medical big data server, and the clinical data acquisition module is further configured to acquire process data and conclusive data of the patient in each clinical department during hospitalization and at discharge within a fixed period of time and process data and conclusive data of the patient after the fixed period of time, and send the process data and the conclusive data to the course data analysis module and the medical big data server.

The fixed period of time is 48 hours, and the authenticity data includes name, age, gender, identity card number, date of birth, marital status, ethnicity, and native place of the patient, the marital status including unmarried, married, divorced, and widowed; the compliance data includes recorded international disease code, a name of a present medical history, a name of a principal diagnostic disease, and a diagnostic scheme; the process data includes medications and test items of the patient during hospitalization and their corresponding expenses, and a name of an operation for the patient during hospitalization; and the conclusive data includes a total amount paid by the patient during hospitalization and the condition of the patient at discharge. The above-mentioned authenticity data, compliance data, process data, and conclusive data are automatically acquired from the patient at admission, during hospitalization and at discharge, or manually entered by medical staff after the patient dictates to the medical staff, or manually entered by medical staff according to clinical treatment situations. All of the authenticity data, compliance data, process data, and conclusive data within the fixed period of time may need to be rectified, and then qualified through rectifications.

The authenticity data and the compliance data of the patient in each clinical department at admission, and process data and conclusive data of the patient during hospitalization and at discharge are acquired, such that authenticity data, compliance data, process data, and conclusive data are comprehensively acquired in admission, hospitalization, and discharge links of medical clinical data quality management, which is conducive to implementing multi-link classified acquisition of clinical medical behaviors, thereby facilitating subsequent dynamic and orderly quality analysis and control of clinical data.

The admission data analysis module is configured to perform authenticity analysis and processing on the authenticity data of the patient in each clinical department at admission within the fixed period of time and the authenticity data of the patient after the fixed period of time to obtain an authenticity factor for the clinical department, and send the authenticity factor to the medical record quality inspection module, and the admission data analysis module is further configured to perform compliance analysis and processing on the compliance data of the patient in each clinical department at admission within the fixed period of time and the compliance data of the patient after the fixed period of time to obtain a compliance factor for the clinical department, and send the compliance factor to the medical record quality inspection module.

The mistakes in the authenticity data include incorrect filling, omissions, and filling in wrong items; and the violations in the compliance data include inconsistency between the international disease code and international classification of diseases ICD-10, mismatch between the present medical history and an actual medical history of the patient, inconsistency between the name of the principal diagnostic disease and a name of a disease to be treated, and mismatch between a name of an operation, an item to be tested, or a name of a drug to be used in the diagnostic scheme and the disease to be treated.

A Specific Process of the Authenticity Analysis and Processing is as Follows:

in step 1, comparing the authenticity data of the patient in each clinical department at admission within the fixed period of time with the authenticity data of the patient after the fixed period of time, to obtain a frequency of occurrence of mistakes, an average time for rectifying mistakes for qualification, and a number of completions mistakes are rectified for qualification of the authenticity data; and in step 2, marking the frequency of occurrence of mistakes, the average time for rectifying mistakes for qualification, and the number of completions mistakes are rectified for qualification of the authenticity data as $Z_{pi}$, $Z_{gi}$, and $Z_{ci}$, respectively, where $i=1, \ldots, n$, and n is a positive integer greater than 1; and performing processing according to a formula $$Zsi = \alpha \sqrt[3]{(a1 \times Zpi)^2 + (a2 \times Zgi)^2 + (a3 \times Zci)^2} \times (Zpi + Zgi + Zci)$$

to obtain an authenticity factor Zsi for each clinical department, where α is a correction factor and α=0.957, a1, a2, and a3 are all preset weight coefficients, a1>a2>a3>0, and a1+a2+a3=3.189.

It should be noted that a greater apparent value of an authenticity factor indicates a poorer quality of authenticity data of a corresponding clinical department.

A Specific Process of the Compliance Analysis and Processing is as Follows:
  in step 1, comparing the compliance data of the patient in each clinical department at admission within the fixed period of time with the compliance data of the patient after the fixed period of time, to obtain a frequency of occurrence of violations, an average time for rectifying violations for qualification, and a number of completions violations are rectified for qualification of the compliance data; and
  in step 2, marking the frequency of occurrence of violations, the average time for rectifying violations for qualification, and the number of completions violations are rectified for qualification of the compliance data as Hpi, Hsi, and Hci, respectively, where i=1, ..., n, and n is a positive integer greater than 1; and performing processing according to a formula $$Hgi = \beta \sqrt[3]{(b1 \times Hpi)^2 + (b2 \times Hsi)^2 + (b3 \times Hci)^2} \times (Hpi + Hsi + Hci)$$

to obtain a compliance factor Hgi for each clinical department, where β is a correction factor and β=0.986, b1, b2, and b3 are all preset weight coefficients, b1>b2>b3>0, and b1+b2+b3=4.219.

It should be noted that a greater apparent value of a compliance factor indicates a poorer quality of compliance data of a corresponding clinical department.

The course data analysis module is configured to perform process analysis and processing on the process data of the patient in each clinical department during hospitalization and at discharge within the fixed period of time and the process data of the patient after the fixed period of time to obtain a process factor for the clinical department, and send the process factor to the operating quality inspection module, and the course data analysis module is further configured to perform conclusive analysis and processing on the conclusive data of the patient in each clinical department during hospitalization and at discharge within the fixed period of time and the conclusive data of the patient after the fixed period of time to obtain a conclusion factor for the clinical department, and send the conclusion factor to the quality inspection module.

The errors in the process data include inconsistency between the medications as well as the test items of the patient during hospitalization and their corresponding expenses, and inconsistency between the name of the operation for the patient during hospitalization and an official name of the operation; and the problems in the conclusive data include inconsistency between the total amount paid by the patient during hospitalization and an actual calculated total payment amount, and nonconformity of records of the patient's condition at discharge with writing specifications.

A Specific Process of the Process Analysis and Processing is as Follows:
  in step 1, comparing the process data of the patient in each clinical department during hospitalization and at discharge within the fixed period of time with the process data of the patient after the fixed period of time, to obtain a total number of occurrences of errors, a total time for rectifying errors for qualification, and a number of completions errors are rectified for qualification of the process data; and
  in step 2, marking the total number of occurrences of errors, the total time for rectifying errors for qualification, and the number of completions errors are rectified for qualification of the process data as Gci, Gsi, and Ghi, respectively, where i=1, ..., n, and n is a positive integer greater than 1; and performing processing according to a formula $$Gzi = \delta \sqrt[3]{\left(\frac{Gci}{c1}\right)^2 + \left(\frac{Gsi}{c2}\right)^2 + \left(\frac{Ghi}{c3}\right)^2}$$

to obtain a process factor Gzi for each clinical department, where δ is a correction factor and δ=0.925, c1, c2, and c3 are all preset weight coefficients, c1>c2>c3>0, and c1+c2+c3=6.284.

It should be noted that a greater apparent value of a process factor indicates a poorer quality of process data of a corresponding clinical department.

A Specific Process of the Conclusive Analysis and Processing is as Follows:
  in step 1, comparing the conclusive data of the patient in each clinical department during hospitalization and at discharge within the fixed period of time with the conclusive data of the patient after the fixed period of time, to obtain a total number of occurrences of problems, a total time for rectifying problems for qualification, and a number of completions problems are rectified for qualification of the conclusive data; and
  in step 2, marking the total number of occurrences of problems, the total time for rectifying problems for qualification, and the number of completions problems are rectified for qualification of the conclusive data as Jci, Jsi, and Jhi, respectively, where i=1, ..., n, and n is a positive integer greater than 1; and performing processing according to a formula $$Jzi = \varepsilon \sqrt[3]{\left(\frac{Jci}{d1}\right)^2 + \left(\frac{Jsi}{d2}\right)^2 + \left(\frac{Jhi}{d3}\right)^2}$$

to obtain a conclusion factor Jzi for each clinical department, where F is a correction factor and ε=0.937, d1, d2, and d3 are all preset weight coefficients, d1>d2>d3>0, and d1+d2+d3=4.876.

It should be noted that a greater apparent value of a conclusion factor indicates a poorer quality of conclusive data of a corresponding clinical department.

The medical record quality inspection module is configured to process the authenticity factor Zsi and the compliance factor Hgi of the clinical department according to a formula $$ZH = \frac{\lambda(n-1)}{\sum_{i=1}^{n} \sqrt{(e1 \times Zsi) + (e2 \times Hgi)}}$$

to obtain a medical record quality coefficient ZH, and compare the medical record quality coefficient ZH with a threshold thereof, and output a medical record qualification signal when the medical record quality coefficient is greater than the threshold thereof, and output a medical record disqualification signal and send the medical record disqualification signal to the medical big data server when the medical record quality coefficient is less than or equal to the threshold thereof, where $\lambda$ is a correction factor and $\lambda=1.387$, e1 and e2 are both preset weight coefficients, e1>e2>0, and e1+e2=1.843. It should be noted that a greater apparent value of a medical record quality coefficient indicates a better quality of data of a patient at admission in a clinical department.

The authenticity analysis and processing are performed on the authenticity data of the patient in the clinical department at admission to obtain the authenticity factor reflecting the quality of the authenticity data; the compliance analysis and processing are performed on the compliance data of the patient in the clinical department at admission to obtain the compliance factor reflecting the quality of the compliance data; and the medical record quality coefficient reflecting the quality of clinical data at admission is obtained by performing integration and processing on the authenticity factor and the compliance factor, and the medical record qualification signal or the medical record disqualification signal is output after the medical record quality coefficient is compared with the threshold thereof. From the perspectives of authenticity and compliance, the quality of clinical data at admission is reflected truly and reliably, and medical errors and costs are reduced at the front end of quality management.

The operating quality inspection module is configured to process the process factor Gzi and the conclusion factor Jzi of the clinical department according to a formula $$GJ = \frac{\mu(n-1)}{\sum_{i=1}^{n} \sqrt{(f1 \times Gzi) + (f2 \times Jzi)}}$$

to obtain an operating quality coefficient GJ, and compare the operating quality coefficient GJ with a threshold thereof, and output an operating qualification signal when the operating quality coefficient is greater than the threshold thereof, and output an operating disqualification signal and send the operating disqualification signal to the medical big data server when the operating quality coefficient is less than or equal to the threshold thereof, where is a correction factor and $\mu=1.185$, f1 and f2 are both preset weight coefficients, f1>f2>0, and f1+f2=2.527. It should be noted that a greater apparent value of an operating quality coefficient indicates a better quality of data of a patient during hospitalization and at discharge in a clinical department.

The process analysis and processing are performed on the process data of the patient in the clinical department during hospitalization and at discharge to obtain the process factor reflecting the quality of the process data; the conclusive analysis and processing are performed on the conclusive data of the patient during hospitalization and at discharge to obtain the conclusion factor reflecting the quality of the conclusive data; and integration and processing are performed on the process factor and the conclusion factor to obtain the operating quality coefficient reflecting the quality of clinical data during hospitalization and at discharge, and after the operating quality coefficient is compared with the threshold thereof, the operating qualification signal or the operating disqualification signal is output. From the perspectives of process and conclusion, the quality of clinical data during hospitalization and at discharge is reflected truly and reliably, and medical errors and costs are reduced at the middle link and tail end of quality management.

The medical big data server is configured to multiply a medical record quality coefficient corresponding to the medical record disqualification signal by an operating quality coefficient corresponding to the operating disqualification signal to obtain a comprehensive quality coefficient, and compare the comprehensive quality coefficient with a preset range thereof, and perform no processing when the comprehensive quality coefficient is greater than a maximum value in the preset range thereof, output a second-level quality control signal when the comprehensive quality coefficient is within the preset range thereof, and output a first-level quality control signal when the comprehensive quality coefficient is less than a minimum value in the preset range thereof.

It should be noted that a greater apparent value of a comprehensive quality coefficient indicates a better quality of comprehensive clinical data of a clinical department.

The medical record quality coefficient and the operating quality coefficient are processed to obtain the comprehensive quality coefficient, and different levels of quality control signals are output after the comprehensive quality coefficient is compared with the preset range thereof, such that when both a medical record signal and an operating signal indicate disqualification, a matching quality control signal is precisely output, which facilitates taking corresponding measures for rectification.

The historical quality analysis module is configured to retrieve the comprehensive quality coefficient from the medical big data server, generate a histogram and a line graph for unit time-comprehensive quality coefficient with the unit time as the abscissa and the comprehensive quality coefficient as the ordinate, and send the histogram and the line graph to a mobile terminal, and the historical quality analysis module is further configured to calculate a rate of change in the comprehensive quality coefficient in adjacent unit time, and send the rate of change to the quality evaluation module, where the unit time is selected to be 48 hours.

The quality evaluation module is configured to match the rate of change in the comprehensive quality coefficient in adjacent unit time with a rate of change evaluation table stored in the quality evaluation module, to obtain a quality inspection evaluation result. In the rate of change evaluation table, when the rate of change is greater than 20%, the quality inspection evaluation result indicates excellent; when the rate of change is between 10% and 20%, the quality inspection evaluation result indicates good; when the rate of change is between 0% and 10%, the quality inspection evaluation result indicates pass; when the rate of change is between −10% and 0, the quality inspection evaluation result indicates fail; and when the rate of change is less than −10%, the quality inspection evaluation result indicates poor.

The histogram and the line graph of unit time-comprehensive quality coefficient intuitively reflect the change trend of comprehensive quality of medical clinical data per unit time; and the quality inspection evaluation result is obtained by performing matching with the rate of change evaluation table, such that scoring and rectification are performed depending on quality inspection evaluation results, thereby reducing the rate of error in clinical data.

The above-mentioned preset weight coefficients are used to balance proportions by weight of all the data in the formula calculations, so as to bring the accuracy in the calculation results. The magnitude of the coefficient is to quantify each parameter to obtain a specific value, so as to facilitate subsequent comparison. The magnitude of the coefficient depends on the amount of sample data and a corresponding weight factor coefficient preliminarily set by those skilled in the art for each set of sample data, as long as it does not affect a proportional relationship between the parameters and the quantified values.

Each of the above formulas is obtained by acquiring a large amount of data for software simulation and selecting one formula close to a real value. The coefficients in the formula are set by those skilled in the art according to actual situations;

for example, in the formula:

$$Gzi = \delta \sqrt[3]{\left(\frac{GCi}{c1}\right)^2 + \left(\frac{Gsi}{c2}\right)^2 + \left(\frac{Gci}{c3}\right)^2},$$

$c2>c1>c3>0$ and $c1+c2+c3=6.284$. A plurality of sets of sample data are acquired by those skilled in the art and a corresponding preset weight coefficient is set for each set of sample data. The preset weight coefficients and the acquired sample data are substituted into the formula, any three formulas form a ternary quadratic equation system, and the calculated coefficients are screened and averaged, to obtain the values 2.168, 2.826, and 1.290 of $c1$, $c2$, and $c3$, respectively.

Embodiment 2

Figure 2:
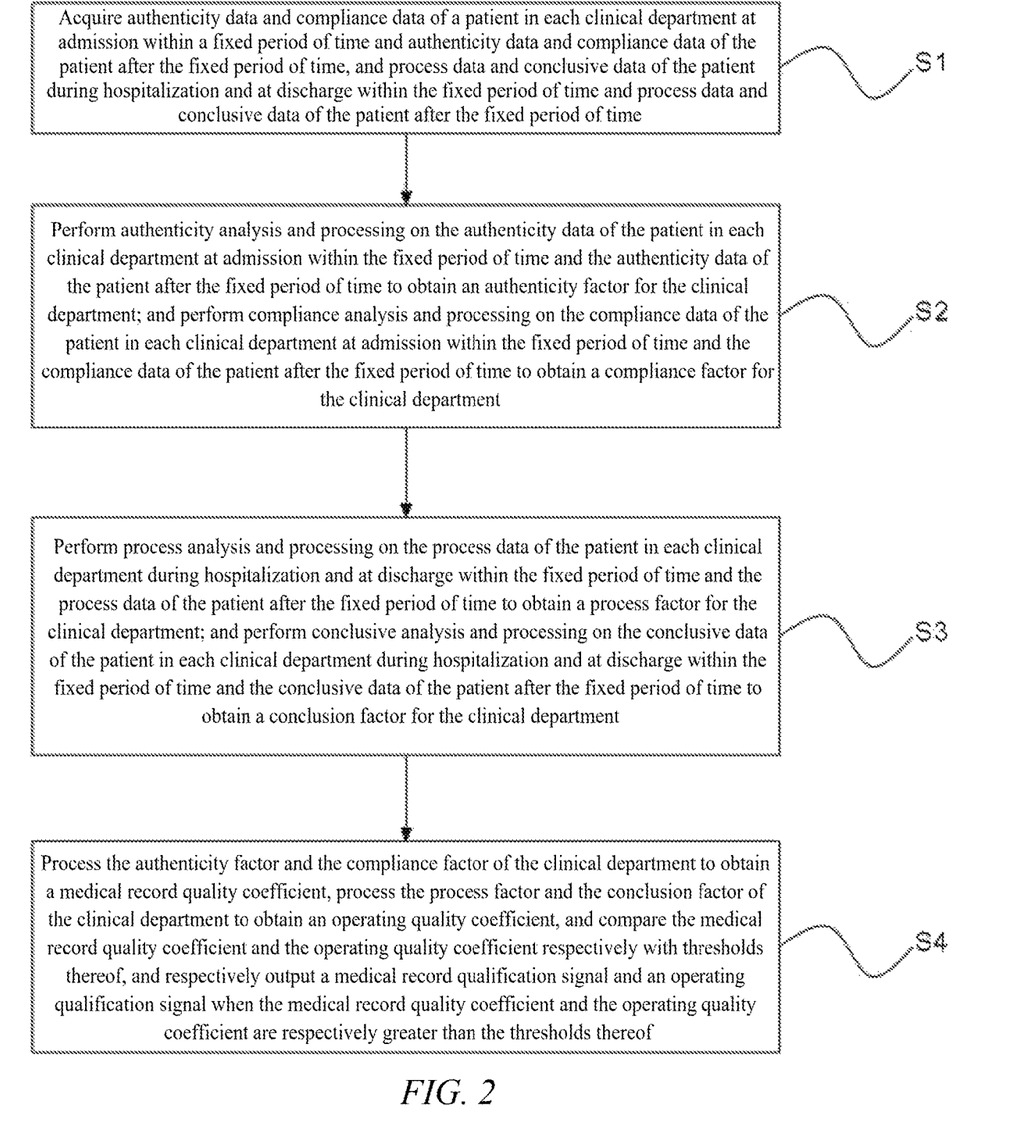
FIG. 2 is a flowchart of a medical clinical data quality analysis method according to Embodiment 2 of the present invention.

As shown in FIG. 2, this embodiment provides a medical clinical data quality analysis method based on big data, which is applied to the medical clinical data quality analysis system in Embodiment 1. The method includes the following steps:
- step S1: acquiring authenticity data and compliance data of a patient in each clinical department at admission within a fixed period of time and authenticity data and compliance data of the patient after the fixed period of time, and process data and conclusive data of the patient during hospitalization and at discharge within the fixed period of time and process data and conclusive data of the patient after the fixed period of time;
- step S2: performing authenticity analysis and processing on the authenticity data of the patient in each clinical department at admission within the fixed period of time and the authenticity data of the patient after the fixed period of time to obtain an authenticity factor for the clinical department, and performing compliance analysis and processing on the compliance data of the patient in each clinical department at admission within the fixed period of time and the compliance data of the patient after the fixed period of time to obtain a compliance factor for the clinical department;
- step S3: performing process analysis and processing on the process data of the patient in each clinical department during hospitalization and at discharge within the fixed period of time and the process data of the patient after the fixed period of time to obtain a process factor for the clinical department, and performing conclusive analysis and processing on the conclusive data of the patient in each clinical department during hospitalization and at discharge within the fixed period of time and the conclusive data of the patient after the fixed period of time to obtain a conclusion factor for the clinical department; and
- step S4: processing the authenticity factor and the compliance factor of the clinical department to obtain a medical record quality coefficient, processing the process factor and the conclusion factor of the clinical department to obtain an operating quality coefficient, and comparing the medical record quality coefficient and the operating quality coefficient respectively with thresholds thereof, and respectively outputting a medical record qualification signal and an operating qualification signal when the medical record quality coefficient and the operating quality coefficient are respectively greater than the thresholds thereof.

According to the medical clinical data quality analysis method based on big data in this embodiment, authenticity analysis is performed on the authenticity data at admission to obtain the authenticity factor, and compliance analysis is performed on the compliance data at admission to obtain the compliance factor; process analysis is performed on the process data during hospitalization and at discharge to obtain the process factor, and conclusive analysis is performed on the conclusive data during hospitalization and at discharge to obtain the conclusion factor; and the authenticity factor and the compliance factor are processed to obtain the medical record quality coefficient, and the process factor and the conclusion factor are processed to obtain the operating quality coefficient. After the medical record quality coefficient and the operating quality coefficient are respectively greater than the thresholds thereof, the medical record qualification signal and the operating qualification signal are respectively output.

Embodiment 3

Figure 3:
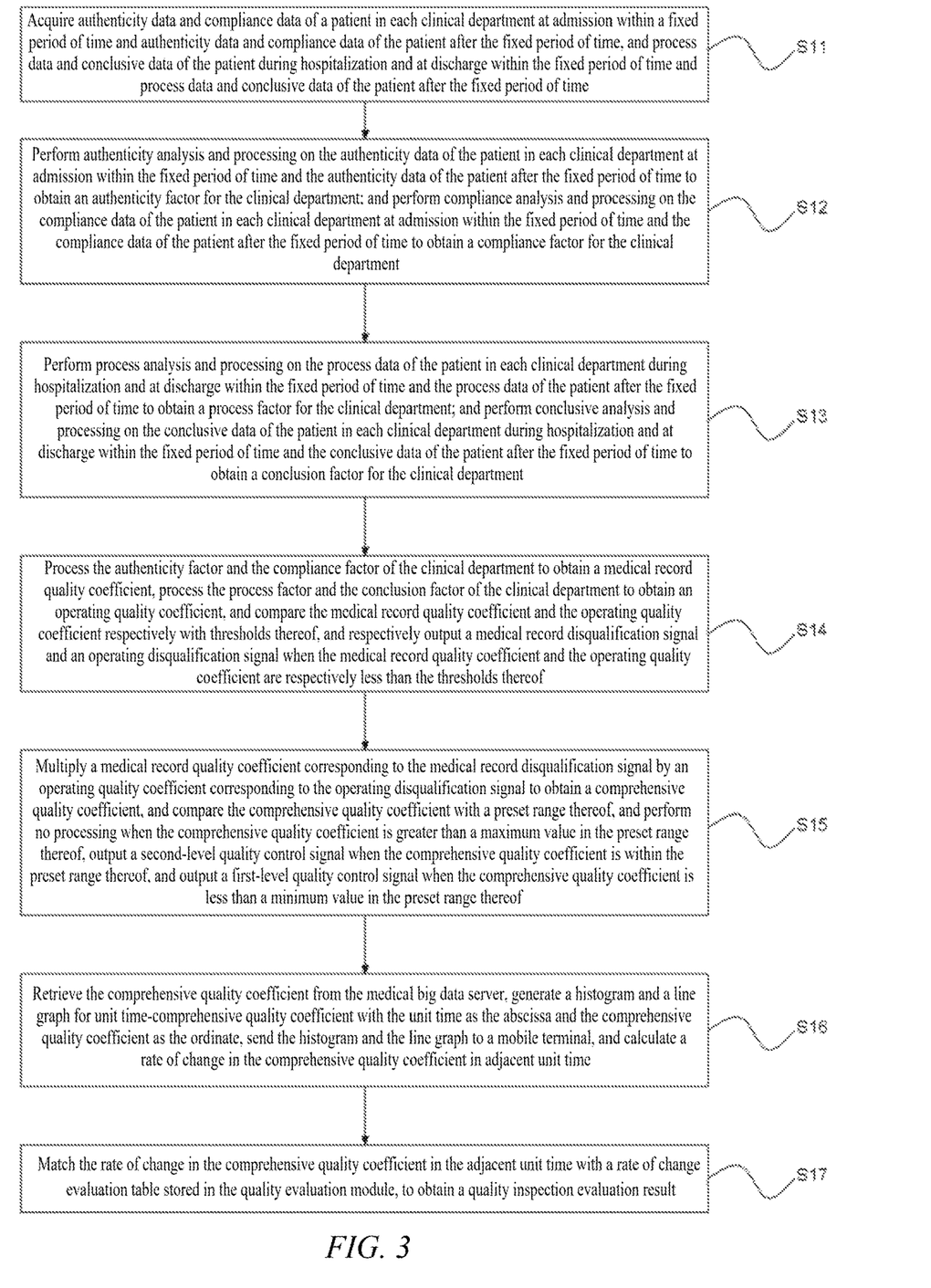
FIG. 3 is a flowchart of a medical clinical data quality analysis method according to Embodiment 3 of the present invention.

As shown in FIG. 3, this embodiment provides a medical clinical data quality analysis method based on big data, which is applied to the medical clinical data quality analysis system in Embodiment 1. The method includes steps S11 to S17, where steps S11 to S13 are the same as steps S1 to S3 in Embodiment 2, and steps S14 to S17 are specifically as follows:
- step S14: processing the authenticity factor and the compliance factor of the clinical department to obtain a medical record quality coefficient, processing the process factor and the conclusion factor of the clinical department to obtain an operating quality coefficient, and comparing the medical record quality coefficient and the operating quality coefficient respectively with the thresholds thereof, and respectively outputting a medical record disqualification signal and an operating disqualification signal when the medical record quality coefficient and the operating quality coefficient are respectively less than the thresholds thereof;
- step S15: multiplying a medical record quality coefficient corresponding to the medical record disqualification signal by an operating quality coefficient corresponding to the operating disqualification signal to obtain a comprehensive quality coefficient, and comparing the comprehensive quality coefficient with a preset range thereof, and performing no processing when the comprehensive quality coefficient is greater than a maximum value in the preset range thereof, outputting a second-level quality control signal when the comprehensive quality coefficient is within the preset range thereof, and outputting a first-level quality control signal when the comprehensive quality coefficient is less than a minimum value in the preset range thereof;

step S16: retrieving the comprehensive quality coefficient from the medical big data server, generating a histogram and a line graph for unit time-comprehensive quality coefficient with the unit time as the abscissa and the comprehensive quality coefficient as the ordinate, sending the histogram and the line graph to a mobile terminal, and calculating a rate of change in the comprehensive quality coefficient in adjacent unit time; and step S17: matching the rate of change in the comprehensive quality coefficient in the adjacent unit time with a rate of change evaluation table stored in the quality evaluation module, to obtain a quality inspection evaluation result.

According to the medical clinical data quality analysis method based on big data in this embodiment, for the medical record disqualification signal and the operating disqualification signal, their corresponding medical record quality coefficient and operating quality coefficient are processed to obtain the comprehensive quality coefficient. The histogram and the line graph of unit time-comprehensive quality coefficient intuitively reflect the change trend of comprehensive quality of medical clinical data per unit time; and the quality inspection evaluation result is obtained by performing matching with the rate of change evaluation table, such that scoring and rectification are performed depending on quality inspection evaluation results, thereby reducing the rate of error in clinical data.

The above content is merely for illustration and description of the structure of the present invention. Various modifications or supplements or replacements in similar manners made by those skilled in the art to the described specific embodiments without departing from the structure of the invention or going beyond the scope defined in the claims should all fall within the scope of protection of the present invention.

In the description of this specification, the description with reference to the terms such as "an embodiment", "an example" and "a specific example" means that specific features, structures, materials or characteristics described with respect to this embodiment or example are included in at least one embodiment or example of the present invention. In this specification, the schematic expressions of the above terms do not necessarily refer to the same embodiments or examples. Furthermore, the specific features, structures, materials, or characteristics described may be combined in a suitable manner in any one or more embodiments or examples.

The preferred embodiments of the present invention disclosed above are only intended to help describe the present invention. The preferred embodiments neither elaborate all the details, nor do they limit the invention only to the specific embodiments. Obviously, according to the content of this specification, many modifications and changes may be made. These embodiments are selected and specifically described in this specification in order to better explain the principles and practical application of the present invention, so that those skilled in the art can well understand and use the present invention. The present invention is limited only by the claims and full scope and equivalents thereof.

What is claimed is:

1. A medical clinical data quality analysis system based on big data, comprising a clinical data acquisition module, an admission data analysis module, a course data analysis module, a medical record quality inspection module, an operating quality inspection module, and a medical big data server, wherein the clinical data acquisition module is configured to acquire authenticity data and compliance data of a patient in each clinical department at admission within a fixed period of time and authenticity data and compliance data of the patient after the fixed period of time, and send the authenticity data and the compliance data to the admission data analysis module and the medical big data server, and the clinical data acquisition module is further configured to acquire process data and conclusive data of the patient in each clinical department during hospitalization and at discharge within a fixed period of time and process data and conclusive data of the patient after the fixed period of time, and send the process data and the conclusive data to the course data analysis module and the medical big data server;

the admission data analysis module is configured to perform authenticity analysis and processing on the authenticity data of the patient in each clinical department at admission within the fixed period of time and the authenticity data of the patient after the fixed period of time to obtain an authenticity factor for the clinical department, and send the authenticity factor to the medical record quality inspection module, and the admission data analysis module is further configured to perform compliance analysis and processing on the compliance data of the patient in each clinical department at admission within the fixed period of time and the compliance data of the patient after the fixed period of time to obtain a compliance factor for the clinical department, and send the compliance factor to the medical record quality inspection module, wherein a specific process of the authenticity analysis and processing is as follows:

in step 1, comparing the authenticity data of the patient in each clinical department at admission within the fixed period of time with the authenticity data of the patient after the fixed period of time, to obtain a frequency of occurrence of mistakes, an average time for rectifying mistakes for qualification, and a number of completions mistakes are rectified for qualification of the authenticity data; and in step 2, marking the frequency of occurrence of mistakes, the average time for rectifying mistakes for qualification, and the number of completions mistakes are rectified for qualification of the authenticity data as $Z_{pi}$, $Z_{gi}$, and $Z_{ci}$, respectively, wherein $i=1, \ldots, n$, and n is a positive integer greater than 1; and performing processing according to a formula $Z_{si} = a\sqrt{(a_1 \times Z_{pi})2 + (a_2 \times Z_{gi})2 + (a_3 \times Z_{ci})2} \times (Z_{pi} + Z_{gi} + Z_{ci})$ to obtain an authenticity factor $Z_{si}$ for each clinical department, wherein alpha is a correction factor and alpha=0.957, $a_1$, $a_2$, and $a_3$ are all preset weight coefficients, $a_1 > a_2 > a_3 > 0$, and $a_1 + a_2 + a_3 = 3.189$; and a specific process of the compliance analysis and processing is as follows:

in step 1, comparing the compliance data of the patient in each clinical department at admission within the fixed period of time with the compliance data of the patient after the fixed period of time, to obtain a frequency of occurrence of violations, an average time for rectifying violations for qualification, and a number of completions violations are rectified for qualification of the compliance data; and in step 2, marking the frequency of occurrence of violations, the average time for rectifying violations for qualification, and the number of completions violations are rectified for qualification of the compliance data as Hpi, Hsi, and Hci, respectively, wherein i=1, ..., n, and n is a positive integer greater than 1; and performing processing according to a formula Hgi=/JV(b1×Hpi)2+ (b2×Hsi)2+(b3×Hci)2×(Hpi+Hsi+Hci) to obtain a compliance factor Hgi for each clinical department, wherein beta is a correction factor and beta=0.986, b1, b2, and b3 are all preset weight coefficients, b1>b2>b3>0, and b1+b2+b3=4.219;

the course data analysis module is configured to perform process analysis and processing on the process data of the patient in each clinical department during hospitalization and at discharge within the fixed period of time and the process data of the patient after the fixed period of time to obtain a process factor for the clinical department, and send the process factor to the operating quality inspection module, and the course data analysis module is further configured to perform conclusive analysis and processing on the conclusive data of the patient in each clinical department during hospitalization and at discharge within the fixed period of time and the conclusive data of the patient after the fixed period of time to obtain a conclusion factor for the clinical department, and send the conclusion factor to the quality inspection module, wherein a specific process of the process analysis and processing is as follows:

in step 1, comparing the process data of the patient in each clinical department during hospitalization and at discharge within the fixed period of time with the process data of the patient after the fixed period of time, to obtain a total number of occurrences of errors, a total time for rectifying errors for qualification, and a number of completions errors are rectified for qualification of the process data; and in step 2, marking the total number of occurrences of errors, the total time for rectifying errors for qualification, and the number of completions errors are rectified for qualification of the process data as Gci, Gsi, and Ghi, respectively, wherein i=1, ..., n, and n is a positive integer greater than 1; and performing processing according to a formula to obtain a process factor Gzi for each clinical department, wherein delta is a correction factor and delta=0.925, c1, c2, and c3 are all preset weight coefficients, c1>c2>c3>0, and c1+c2+c3=6.284; and a specific process of the conclusive analysis and processing is as follows:

in step 1, comparing the conclusive data of the patient in each clinical department during hospitalization and at discharge within the fixed period of time with the conclusive data of the patient after the fixed period of time, to obtain a total number of occurrences of problems, a total time for rectifying problems for qualification, and a number of completions problems are rectified for qualification of the conclusive data; and in step 2, marking the total number of occurrences of problems, the total time for rectifying problems for qualification, and the number of completions problems are rectified for qualification of the conclusive data as Jci, Jsi, and Jhi, respectively, wherein i=1, ..., n, and n is a positive integer greater than 1; and performing processing according to a formula J*_(Jci)2 (Jsi)2 (Jhi)2 Zl−c3−d1+−d2+−d3 to obtain a conclusion factor Jzi for each clinical department, wherein epsilon is a correction factor and epsilon=0.937, d1, d2, and d3 are all preset weight coefficients, d1>d2>d3>0, and d1+d2+d3=4.876; the medical record quality inspection module is configured to process the authenticity factor Zsi and the compliance factor Hgi of the clinical department according to a formula A Cn−n ZH=n I·JCelxZsi)+Ce2xHgi) i=I to obtain a medical record quality coefficient ZH, and compare the medical record quality coefficient ZH with a threshold thereof, and output a medical record qualification signal when the medical record quality coefficient is greater than the threshold thereof, and output a medical record disqualification signal and send the medical record disqualification signal to the medical big data server when the medical record quality coefficient is less than or equal to the threshold thereof, wherein lambda is a correction factor and lambda=1.387, e1 and e2 are both preset weight coefficients, e1>e2>0, and e1+e2=1.843;

the operating quality inspection module is configured to process the process factor Gzi and the conclusion factor Jzi of the clinical department according to a formula GJ=---μ_Cn−1)_n I−JCflxG zi)+Cf2xJzi) i=I to obtain an operating quality coefficient GJ, and compare the operating quality coefficient GJ with a threshold thereof, and output an operating qualification signal when the operating quality coefficient is greater than the threshold thereof, and output an operating disqualification signal and send the operating disqualification signal to the medical big data server when the operating quality coefficient is less than or equal to the threshold thereof, wherein mu is a correction factor and mu=1.185, f1 and f2 are both preset weight coefficients, f1>f2>0, and f1+f2=2.527; and the medical big data server is configured to multiply the medical record quality coefficient corresponding to the medical record disqualification signal by the operating quality coefficient corresponding to the operating disqualification signal to obtain a comprehensive quality coefficient, and compare the comprehensive quality coefficient with a preset range thereof, and perform no processing when the comprehensive quality coefficient is greater than a maximum value in the preset range thereof, output a second-level quality control signal when the comprehensive quality coefficient is within the preset range thereof, and output a first-level quality control signal when the comprehensive quality coefficient is less than a minimum value in the preset range thereof.

2. The medical clinical data quality analysis system based on big data according to claim 1, wherein the fixed period of time is 12 hours, 24 hours, 48 hours, or 72 hours, and the authenticity data comprises name, age, gender, identity card number, date of birth, marital status, ethnicity, and native place of the patient, the marital status comprising unmarried, married, divorced, and widowed; and the compliance data comprises recorded international disease code, a name of a present medical history, a name of a principal diagnostic disease, and a diagnostic scheme.

3. The medical clinical data quality analysis system based on big data according to claim 2, wherein the mistakes in the authenticity data comprise incorrect filling, omissions, and filling in wrong items; and the violations in the compliance data comprise inconsistency between the international disease code and international classification of diseases ICD-10, mismatch between the present medical history and an actual medical history of the patient, inconsistency between the name of the principal diagnostic disease and a name of a disease to be treated, and mismatch between a name of an operation, an item to be tested, or a name of a drug to be used in the diagnostic scheme and the disease to be treated.

4. The medical clinical data quality analysis system based on big data according to claim 1, wherein the process data comprises medications and test items of the patient during hospitalization and their corresponding expenses, and a name of an operation for the patient during hospitalization; and the conclusive data comprises a total amount paid by the patient during hospitalization and the condition of the patient at discharge.

5. The medical clinical data quality analysis system based on big data according to claim 4, wherein the errors in the process data comprise inconsistency between the medications as well as the test items of the patient during hospitalization and their corresponding expenses, and inconsistency between the name of the operation for the patient during hospitalization and an official name of the operation; and the problems in the conclusive data comprise inconsistency between the total amount paid by the patient during hospitalization and an actual calculated total payment amount, and nonconformity of records of the patient's condition at discharge with writing specifications.

6. The medical clinical data quality analysis system based on big data according to claim 1, wherein the medical clinical data quality analysis system further comprises a historical quality analysis module and a quality evaluation module, wherein the historical quality analysis module is configured to retrieve the comprehensive quality coefficient from the medical big data server, generate a histogram and a line graph for unit time comprehensive quality coefficient with the unit time as the abscissa and the comprehensive quality coefficient as the ordinate, and send the histogram and the line graph to a mobile terminal, and the historical quality analysis module is further configured to calculate a rate of change in the comprehensive quality coefficient in adjacent unit time, and send the rate of change to the quality evaluation module; and the quality evaluation module is configured to match the rate of change in the comprehensive quality coefficient in adjacent unit time with a rate of change evaluation table stored in the quality evaluation module, to obtain a quality inspection evaluation result.

7. The medical clinical data quality analysis system based on big data according to claim 6, wherein the unit time is selected from 12 hours, 24 hours, 48 hours, or 72 hours; and in the rate of change evaluation table, when the rate of change is greater than 20%, the quality inspection evaluation result indicates excellent; when the rate of change is between 10% and 20%, the quality inspection evaluation result indicates good; when the rate of change is between 0% and 10%, the quality inspection evaluation result indicates pass; when the rate of change is between −10% and 0%, the quality inspection evaluation result indicates fail; and when the rate of change is less than −10%, the quality inspection evaluation result indicates poor.

\* \* \* \* \*